(12) United States Patent
Lau et al.

(10) Patent No.: US 11,938,285 B2
(45) Date of Patent: Mar. 26, 2024

(54) STOP-MOVEMENT DEVICE FOR ELONGATED MEDICAL ASSEMBLY

(71) Applicant: Boston Scientific Medical Device Limited, Galway (IE)

(72) Inventors: Kaylie Lau, Toronto (CA); Gareth Davies, Toronto (CA); Eduardo Moriyama, Richmond (CA); Christian Balkovec, Burlington (CA)

(73) Assignee: Boston Scientific Medical Device Limited, Ballybrit (IE)

( * ) Notice: Subject to any disclaimer, the term of this patent is extended or adjusted under 35 U.S.C. 154(b) by 185 days.

(21) Appl. No.: 17/346,422

(22) Filed: Jun. 14, 2021

(65) Prior Publication Data

US 2021/0393925 A1 Dec. 23, 2021

Related U.S. Application Data

(60) Provisional application No. 63/040,037, filed on Jun. 17, 2020.

(51) Int. Cl.
*A61M 25/09* (2006.01)
*A61B 17/00* (2006.01)
*A61B 17/34* (2006.01)

(52) U.S. Cl.
CPC ....... *A61M 25/09* (2013.01); *A61B 17/00234* (2013.01); *A61B 17/3478* (2013.01); *A61B 2017/00243* (2013.01); *A61B 2017/003* (2013.01); *A61B 2017/347* (2013.01); *A61M 2025/09116* (2013.01); *A61M 2025/09175* (2013.01)

(58) Field of Classification Search
CPC . A61B 17/34; A61B 17/3403; A61B 17/3417; A61B 17/00234; A61B 2017/347; A61B 2017/003; A61M 2025/09175
See application file for complete search history.

(56) References Cited

U.S. PATENT DOCUMENTS

| | | |
|---|---|---|
| 175,254 A | 3/1876 | Oberly |
| 827,626 A | 7/1906 | Gillet |
| 848,711 A | 4/1907 | Weaver |
| 1,072,954 A | 9/1913 | Junn |
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | De Master |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |
| 3,595,239 A | 7/1971 | Petersen |
| 4,129,129 A | 12/1978 | Amrine |
| 4,244,362 A | 1/1981 | Anderson |
| 4,401,124 A | 8/1983 | Guess et al. |

(Continued)

*Primary Examiner* — Shaun L David
*Assistant Examiner* — Rachael L Geiger
(74) *Attorney, Agent, or Firm* — Nelson Mullins Riley & Scarborough LLP

(57) ABSTRACT

A stop-movement device is configured to be mounted to a first elongated medical assembly and a second elongated medical assembly. The stop-movement device has a body configured to stop, at least in part, relative movement between the second elongated medical assembly and the first elongated medical assembly.

16 Claims, 7 Drawing Sheets

(56) References Cited

U.S. PATENT DOCUMENTS

| | | |
|---|---|---|
| 4,639,252 A | 1/1987 | Kelly et al. |
| 4,641,649 A | 2/1987 | Walinsky et al. |
| 4,669,467 A | 6/1987 | Willett et al. |
| 4,682,596 A | 7/1987 | Bales et al. |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,149,324 A * | 9/1992 | Clawson ............. A61B 17/34 604/110 |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,626,607 A | 4/1997 | Malecki et al. |
| 5,667,488 A | 9/1997 | Lundquist et al. |
| 5,673,695 A | 10/1997 | McGee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |
| 6,117,131 A | 9/2000 | Taylor |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |

(56) References Cited

U.S. PATENT DOCUMENTS

| | | |
|---|---|---|
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,828,796 B2 | 11/2010 | Wong et al. |
| 7,900,928 B2 | 3/2011 | Held et al. |
| 8,192,425 B2 | 6/2012 | Mirza et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McLntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | McGuckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Violante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1 | 3/2005 | Hartley et al. |
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0262431 A1* | 10/2008 | Anderson ......... A61M 25/0606 604/165.01 |
| 2008/0275439 A1 | 11/2008 | Francischelli et al. |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2011/0046619 A1 | 2/2011 | Ducharme |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0206987 A1 | 7/2014 | Urbanski et al. |
| 2014/0296769 A1 | 10/2014 | Hyde et al. |
| 2015/0272618 A1* | 10/2015 | Fung ............... A61B 17/00234 606/185 |
| 2016/0220741 A1 | 8/2016 | Garrison et al. |
| 2019/0021763 A1 | 1/2019 | Zhou et al. |
| 2019/0247035 A1 | 8/2019 | Gittard et al. |
| 2021/0162177 A1 | 6/2021 | Weise et al. |

* cited by examiner

STOP-MOVEMENT DEVICE FOR ELONGATED MEDICAL ASSEMBLY

TECHNICAL FIELD

This document relates to the technical fields of (A) an apparatus (for use with a first elongated medical assembly and a second elongated medical assembly) including a stop-movement device; and (B) an apparatus including a synergistic combination of a first elongated medical assembly, a second elongated medical assembly and a stop-movement device; and (C) a method of operating a stop-movement device with a first elongated medical assembly and a second elongated medical assembly; and (D) an apparatus (for use with an elongated dilator assembly and an elongated needle assembly) including a stop-movement device; and (E) an apparatus including a synergistic combination of an elongated dilator assembly, an elongated needle assembly and a stop-movement device; and (F) a method of operating a stop-movement device with an elongated dilator assembly and an elongated needle assembly.

BACKGROUND

Known medical devices are configured to facilitate a medical procedure, and help healthcare providers diagnose and/or treat medical conditions of sick patients.

SUMMARY

It will be appreciated that there exists a need to mitigate (at least in part) at least one problem associated with the existing (known) dilators and/or guidewires, etc., (also called the existing technology). After much study of, and experimentation with, the existing (known) dilators and/or guidewires, etc., an understanding (at least in part) of the problem and its solution have been identified (at least in part) and are articulated (at least in part) as follows:

Referring to the embodiment as depicted in FIG. 1 (known puncture device and the hub of the dilator), physicians may use a known technique (such as, the two-finger technique) wherein a finger is placed between a puncture device 800 (also called a needle), and a hub 801 of the dilator and the elongated sheath assembly 804. As depicted in FIG. 1, the handling of the puncture device 800 is performed by using the known two-finger technique (by a single hand 802). This technique may be awkward to execute (may waste valuable procedural time), and/or may lead to inadvertent injury to the patient and/or the surgeon, etc. For instance, when performing a transseptal puncture procedure, it may be necessary to maintain the puncture device 800 in place with respect to the hub 801 of the dilator and elongated sheath assembly 804. The puncture device 800 may have a hub 806 and may include a mechanical needle and/or a radio-frequency needle, etc. For example, when tenting the fossa ovalis (of the heart or any biological feature of the patient), the puncture device 800 may be positioned proximal to a tip of the elongated dilator assembly. If this is not the case, inadvertent (unwanted) puncture of the fossa ovalis and/or unwanted damage to other cardiac structures (biological features) may be possible.

What may be desired is an assembly configured to allow a user (a physician, etc.) to avoid usage of the known 2-finger technique. What may be desired is an assembly configured to allow the user to secure a puncture device during a procedure. What may be desired is an assembly configured to provide a better way to improve, at least in part, safety for a user using a procedure, such as a transseptal technique, etc.

To mitigate, at least in part, at least one problem associated with the existing technology, there is provided (in accordance with a major aspect) an apparatus. The apparatus is for (is configured to be utilized with) a first elongated medical assembly and a second elongated medical assembly configured to be receivable, at least in part, inside and movable, at least in part, along the first elongated medical assembly. The apparatus includes and is not limited to (comprises) a stop-movement device configured to be mounted to the first elongated medical assembly and the second elongated medical assembly. This is done, preferably, after the second elongated medical assembly, in use, is received, at least in part, inside the first elongated medical assembly. The stop-movement device has a body configured to stop, at least in part, relative movement between the second elongated medical assembly and the first elongated medical assembly. This is done, preferably, after the stop-movement device is mounted to the second elongated medical assembly and first elongated medical assembly.

To mitigate, at least in part, at least one problem associated with the existing technology, there is provided (in accordance with a major aspect) an apparatus. The apparatus is for (is configured to be utilized with) an elongated dilator assembly and an elongated needle assembly configured to be receivable, at least in part, inside and movable, at least in part, along the elongated dilator assembly. The apparatus includes and is not limited to a stop-movement device configured to be mounted to the elongated needle assembly and the elongated dilator assembly. This is done, preferably, after the elongated needle assembly, in use, is received, at least in part, inside the elongated dilator assembly. The stop-movement device has a body configured to stop, at least in part, relative movement between the elongated needle assembly and the elongated dilator assembly. This is done, preferably, after the stop-movement device is mounted to the elongated needle assembly and the elongated dilator assembly.

To mitigate, at least in part, at least one problem associated with the existing technology, there is provided (in accordance with a major aspect) an apparatus. The apparatus includes and is not limited to (comprises) a synergistic combination of an elongated dilator assembly, an elongated needle assembly and a stop-movement device. The elongated needle assembly is configured to be receivable, at least in part, inside and movable, at least in part, along the elongated dilator assembly. The stop-movement device is configured to be mounted to the elongated needle assembly and the elongated dilator assembly; this is done, preferably, after the elongated needle assembly, in use, is received, at least in part, inside the elongated dilator assembly. The stop-movement device has a body configured to stop, at least in part, relative movement between the elongated needle assembly and the elongated dilator assembly; this is done, preferably, after the stop-movement device is mounted to the elongated needle assembly and the elongated dilator assembly.

To mitigate, at least in part, at least one problem associated with the existing technology, there is provided (in accordance with a major aspect) a method. The method is for using the stop-movement device with an elongated dilator assembly and an elongated needle assembly configured to be receivable, at least in part, inside and movable, at least in part, along the elongated dilator assembly. The method includes and is not limited to (comprises) mounting the stop-movement device to the elongated needle assembly and the elongated dilator assembly; this is done, preferably, after the elongated needle assembly, in use, is received, at least in part, inside the elongated dilator assembly. The method also includes stopping relative movement between the elongated needle assembly and the elongated dilator assembly with a body of the stop-movement device; this is done, preferably, after the stop-movement device is mounted to the elongated needle assembly and the elongated dilator assembly.

Other aspects are identified in the claims. Other aspects and features of the non-limiting embodiments may now become apparent to those skilled in the art upon review of the following detailed description of the non-limiting embodiments with the accompanying drawings. This Summary is provided to introduce concepts in simplified form that are further described below in the Detailed Description. This Summary is not intended to identify potentially key features or possible essential features of the disclosed subject matter, and is not intended to describe each disclosed embodiment or every implementation of the disclosed subject matter. Many other novel advantages, features, and relationships will become apparent as this description proceeds. The figures and the description that follow more particularly exemplify illustrative embodiments.

BRIEF DESCRIPTION OF THE DRAWINGS

The non-limiting embodiments may be more fully appreciated by reference to the following detailed description of the non-limiting embodiments when taken in conjunction with the accompanying drawings, in which.

Figure 1:
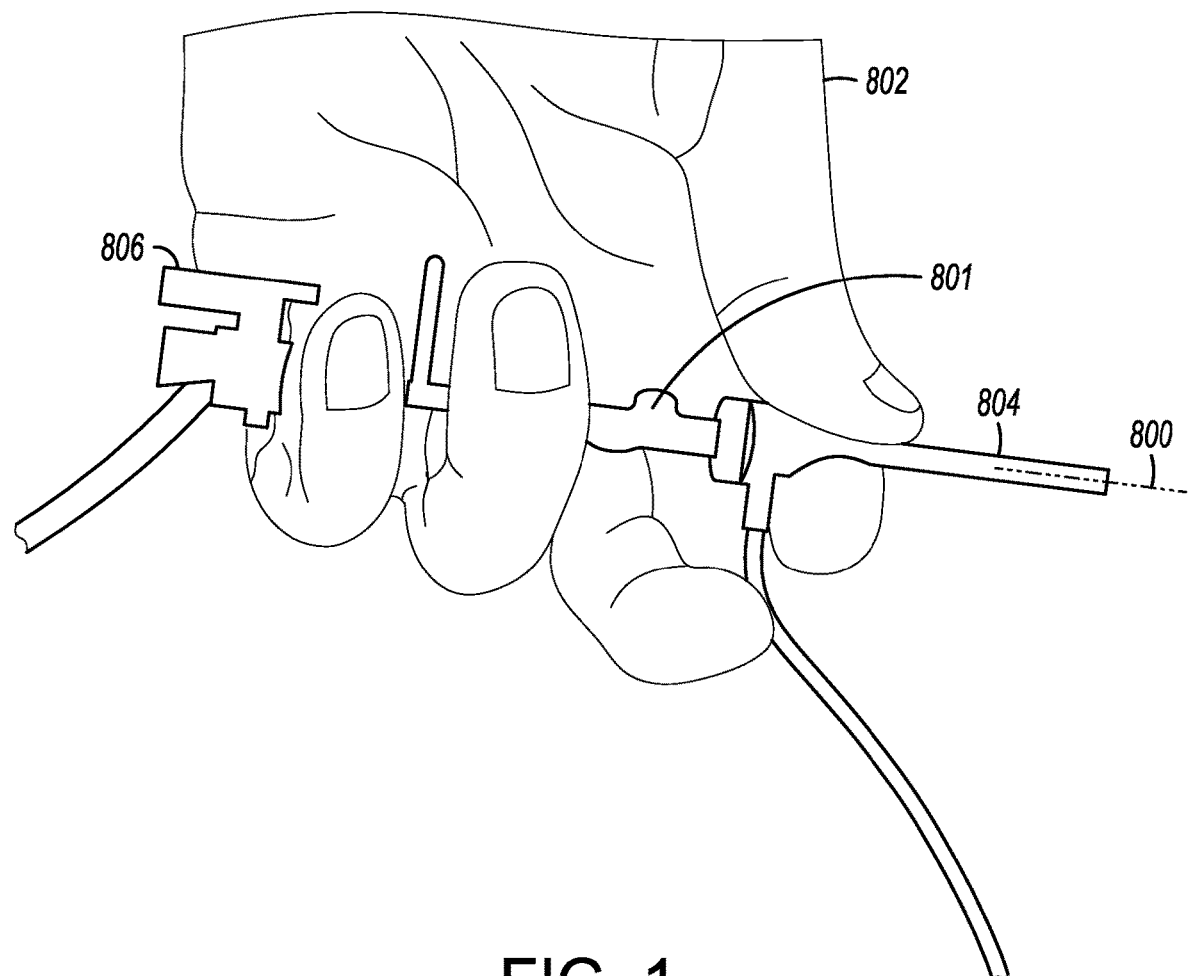
FIG. 1 depicts side view of a known puncture device and the hub of the dilator.

The drawings are not necessarily to scale and may be illustrated by phantom lines, diagrammatic representations, and fragmentary views. In certain instances, details unnecessary for an understanding of the embodiments (and/or details that render other details difficult to perceive) may have been omitted. Corresponding reference characters indicate corresponding components throughout the several figures of the drawings. Elements in the several figures are illustrated for simplicity and clarity and have not been drawn to scale. The dimensions of some of the elements in the figures may be emphasized relative to other elements for facilitating an understanding of the various disclosed embodiments. In addition, common, and well-understood, elements that are useful in commercially feasible embodiments are often not depicted to provide a less obstructed view of the embodiments of the present disclosure.

LISTING OF REFERENCE NUMERALS USED IN THE DRAWINGS

| | |
|---|---|
| elongated medical assembly 100 | dilator hub portion 104 |
| elongated dilator assembly 102 | dilator tip 105 |
| proximal end portion 103 | end section 112 |
| elongated medical assembly 200 | single body member 380 |
| elongated needle assembly 202 | first end face 381 |
| distal puncture device 204 | second end face 382 |
| handle 206 | step 384 |
| stop-movement device 300 | first inner wall surface 391 |
| body 301 | second inner wall surface 392 |
| receiving portal 302 | guidewire assembly 401 |
| first body 311 | sheath assembly 402 |
| second body 312 | first interior zone 501 |
| first body cavity 321 | second interior zone 502 |
| first body groove 322 | first movement direction 601 |
| second body cavity 331 | second movement direction 602 |
| second body groove 332 | axial movement direction 603 |
| first step 341 | puncture device 800 |
| second step 342 | single hand 802 |
| first entrance 351 | elongated sheath assembly 804 |
| second entrance 352 | needle handle 806 |
| first connection protrusion 361 | energy generator 900 |
| second connection protrusion 362 | electrical connection 902 |
| first connection groove 371 | biological feature 904 |
| second connection groove 372 | puncture hole 905 |

DETAILED DESCRIPTION OF THE NON-LIMITING EMBODIMENT(S)

The following detailed description is merely exemplary and is not intended to limit the described embodiments or the application and uses of the described embodiments. As used, the word "exemplary" or "illustrative" means "serving as an example, instance, or illustration." Any implementation described as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure. The scope of the disclosure is defined by the claims. For the description, the terms "upper," "lower," "left," "rear," "right," "front," "vertical," "horizontal," and derivatives thereof shall relate to the examples as oriented in the drawings. There is no intention to be bound by any expressed or implied theory in the preceding Technical Field, Background, Summary or the following detailed description. It is also to be understood that the devices and processes illustrated in the attached drawings, and described in the following specification, are exemplary embodiments (examples), aspects and/or concepts defined in the appended claims. Hence, dimensions and other physical characteristics relating to the embodiments disclosed are not to be considered as limiting, unless the claims expressly state otherwise. It is understood that the phrase "at least one" is equivalent to "a". The aspects (examples, alterations, modifications, options, variations, embodiments and any equivalent thereof) are described regarding the drawings. It should be understood that the disclosure is limited to the subject matter provided by the claims, and that the disclosure is not limited to the particular aspects depicted and described. It will be appreciated that the scope of the meaning of a device configured to be coupled to an item (that is, to be connected to, to interact with the item, etc.) is to be interpreted as the device being configured to be coupled to the item, either directly or indirectly. Therefore, "configured to" may include the meaning "either directly or indirectly" unless specifically stated otherwise.

Figure 2:
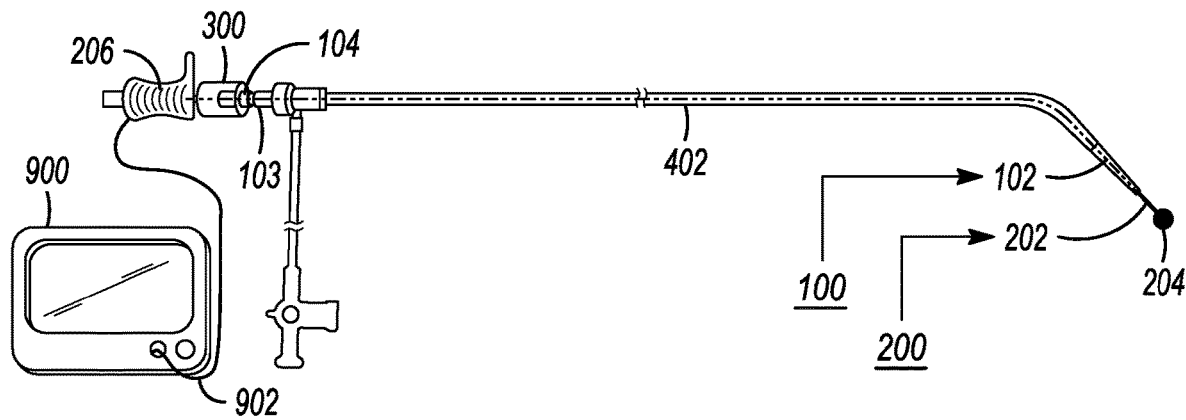
FIG. 2 depicts a side perspective view of an embodiment of a stop-movement device configured to be mounted to an elongated needle assembly and an elongated dilator assembly.

FIG. 2 depicts a side perspective view of an embodiment of a stop-movement device 300 configured to be mounted to an elongated needle assembly 202 and an elongated dilator assembly 102.

Figure 3:
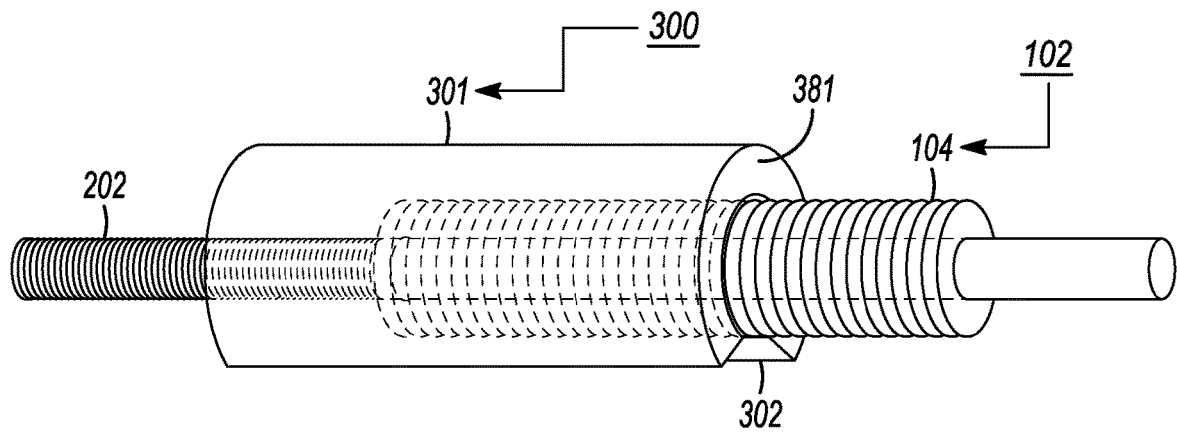
FIG. 3 depicts a close-up side perspective view of an embodiment of the stop-movement device of FIG. 2.

FIG. 3 depicts a close-up side perspective view of an embodiment of the stop-movement device 300 of FIG. 2.

Referring to the embodiments as depicted in FIG. 2 and FIG. 3, it will be appreciated that a first elongated medical assembly 100, a second elongated medical assembly 200 and a stop-movement device 300 may be manufactured, or provided by, separately. For this case, there is provided an apparatus for (configured to be used with) the first elongated medical assembly 100 and the second elongated medical assembly 200 configured to be receivable, at least in part, inside and movable, at least in part, along the first elongated medical assembly 100. The apparatus includes, and is not limited to, a stop-movement device 300 configured to be mounted to the first elongated medical assembly 100 and the second elongated medical assembly 200; this is done, preferably, after the second elongated medical assembly 200, in use, is received, at least in part, inside the first elongated medical assembly 100. The stop-movement device 300 has a body 301 configured to stop, at least in part, relative movement between the second elongated medical assembly 200 and the first elongated medical assembly 100. This is done, preferably, after the stop-movement device 300 is mounted to the second elongated medical assembly 200 and first elongated medical assembly 100.

Referring to the embodiments as depicted in FIG. 2 and FIG. 3, the stop-movement device 300 includes, preferably, SAE (Society of Automotive Engineering) Type 304 Stainless Steel, and any equivalent thereof. SAE Type 304 stainless steel contains both chromium (from between about 15% to about 20%) and nickel (from between about 2% to about 10.5%) metals as the main non-iron constituents.

Referring to the embodiments as depicted in FIG. 2 and FIG. 3, it will be appreciated that an elongated dilator assembly 102, an elongated needle assembly 202 and the stop-movement device 300 may be manufactured, or provided by, separately. The apparatus includes, and is not limited to, a stop-movement device 300 configured to be mounted to the elongated needle assembly 202 and the elongated dilator assembly 102; this is done, preferably, after the elongated needle assembly 202, in use, is received, at least in part, inside the elongated dilator assembly 102.

The stop-movement device 300 has a body 301 configured to stop, at least in part, relative movement between the elongated needle assembly 202 and the elongated dilator assembly 102; this is done, preferably, after the stop-movement device 300 is mounted to the elongated needle assembly 202 and the elongated dilator assembly 102.

Referring to the embodiments as depicted in FIG. 2 and FIG. 3, it will be appreciated that the elongated dilator assembly 102, the elongated needle assembly 202 and the stop-movement device 300 may be manufactured, or provided by, a single entity or company. The apparatus includes and is not limited to a synergistic combination of the elongated dilator assembly 102, the elongated needle assembly 202 and the stop-movement device 300. The stop-movement device 300 is configured to be mounted to the elongated needle assembly 202 and the elongated dilator assembly 102; this is done, preferably, after the elongated needle assembly 202, in use, is received, at least in part, inside the elongated dilator assembly 102. The stop-movement device 300 has a body 301 configured to stop, at least in part, relative movement between the elongated needle assembly 202 and the elongated dilator assembly 102; this is done, preferably, after the stop-movement device 300 is mounted to the elongated needle assembly 202 and the elongated dilator assembly 102.

Referring to the embodiment as depicted in FIG. 2, the elongated dilator assembly 102 is configured to be received in a sheath assembly 402. The elongated dilator assembly 102 includes a proximal end portion 103 that extends from the sheath assembly 402. The dilator hub portion 104 extends from the proximal end portion 103. A handle 206 is attached to the proximal end portion of the elongated needle assembly 202.

Referring to the embodiments as depicted in FIG. 2 and FIG. 3, there is depicted a method (steps) for using the stop-movement device 300 with the elongated dilator assembly 102 and the elongated needle assembly 202. The method includes mounting the stop-movement device 300 to the elongated needle assembly 202 and the elongated dilator assembly 102 after the elongated needle assembly 202, in use, is received, at least in part, inside the elongated dilator assembly 102. The method also includes stopping relative movement between the elongated needle assembly 202 and the elongated dilator assembly 102 with a body 301 of the stop-movement device 300 after the stop-movement device 300 is mounted to the elongated needle assembly 202 and the elongated dilator assembly 102.

Referring to the embodiments as depicted in FIG. 2 and FIG. 3, the elongated needle assembly 202 includes (preferably) a shape-memory material configured to be manipulated and/or deformed followed by a return to the original shape that the shape-memory material was set in (prior to manipulation). Shape-memory materials (SMMs) are known and not further described in detail. Shape-memory materials are configured to recover their original shape from a significant and seemingly plastic deformation in response to application of a particular (predetermined) stimulus (force) to the shape-memory material. This is known as the shape memory effect (SME). Superelasticity (in alloys) may be observed once, or after, the shape-memory material is deformed under the presence (an application) of a stimulus force.

Referring to the embodiments as depicted in FIG. 2 and FIG. 3, the elongated dilator assembly 102 and the elongated needle assembly 202 (including the first elongated medical assembly 100 and the second elongated medical assembly 200) are configured to be inserted into a confined space or tortuous space defined by a living body (the patient).

Referring to the embodiments as depicted in FIG. 2 and FIG. 3, the elongated dilator assembly 102 and the elongated needle assembly 202 (including the first elongated medical assembly 100 and the second elongated medical assembly 200) are (preferably) impermeable by a bodily fluid located in the confined space defined by the living body (of the patient).

Referring to the embodiments as depicted in FIG. 2 and FIG. 3, the elongated dilator assembly 102 and the elongated needle assembly 202 (including the first elongated medical assembly 100 and the second elongated medical assembly 200) include (in accordance with a preferred embodiment) biocompatible material properties suitable for sufficient performance (dielectric strength, thermal performance, insulation and corrosion, water and heat resistance) for safe performance to comply with industrial and regulatory safety standards (or compatible for medical usage). Reference is made to the following publication for consideration in the selection of a suitable material: Plastics in Medical Devices: Properties, Requirements, and Applications; 2nd Edition; author. Vinny R. Sastri; hardcover ISBN: 9781455732012;

published: 21 Nov. 2013; publisher: Amsterdam [Pays-Bas]: Elsevier/William Andrew, [2014].

Referring to the embodiment as depicted in FIG. 2, the elongated needle assembly 202 includes (preferably) a distal puncture device 204.

Referring to the embodiment as depicted in FIG. 2, the distal puncture device 204 includes (preferably) an energy emitting device. The energy emitting device, for instance, may include a radio frequency puncture device, such as the BAYLIS (TRADEMARK) NRG (REGISTERED TRADEMARK) radio frequency needle manufactured by the BAYLIS MEDICAL COMPANY (headquartered in Canada). For the case as depicted in FIG. 2, an energy generator 900 is electrically connected to the distal puncture device 204 via an electrical connection 902 using connection plugs and/or structures that are known and not described in detail. In accordance with another embodiment (known and not depicted), the elongated needle assembly 202 includes (and is not limited to) an elongated needle having a distal tip section presenting a mechanical cutting portion (for this case, the puncture hole may be formed by physically moving the mechanical cutting portion into the biological feature or wall, etc.).

Referring to the embodiment as depicted in FIG. 3, the body 301 (of the stop-movement device 300) includes (preferably) an elastically deformable material defining a receiving portal 302. The receiving portal 302 is aligned coaxially with a longitudinal axis that extends between opposite end sections (faces) of the body 301. The receiving portal 302 (defined by the body 301) is configured to receive, at least in part, and hold onto a portion of the elongated dilator assembly 102 and a portion of the elongated needle assembly 202. Generally, the stop-movement device 300 is configured to selectively receive, at least in part, and hold onto the elongated dilator assembly 102 and the elongated needle assembly 202, and the stop-movement device 300 is configured to selectively release from the elongated dilator assembly 102 and the elongated needle assembly 202. The body 301 has a resilient material. The definition of resilient material may include an elastically deformable material, an elastically resilient material, a sticky material, a friction fitted material, etc. The stop-movement device 300 may be shaped to be friction fitted, at least in part, to a portion of an outer surface of the elongated needle assembly 202. The stop-movement device 300 may be shaped to be friction fitted, at least in part, to a portion of an outer surface of the elongated dilator assembly 102 (such as, to the outer surface of the dilator hub portion 104 of the elongated dilator assembly 102). Friction fitted may include tight fit, malleable, sticky, etc. The stop-movement device 300 is shaped to fit around, at least in part, a portion of an outer diameter of the elongated needle assembly 202. The stop-movement device 300 is shaped to fit around, at least in part, a portion of an outer diameter of the elongated dilator assembly 102 (or the dilator hub portion 104 of the elongated dilator assembly 102). After (or once) the stop-movement device 300 is installed to the elongated dilator assembly 102 and the elongated needle assembly 202, relative movement between the elongated needle assembly 202 and the elongated dilator assembly 102 is prevented or stopped by the stop-movement device 300. The stop-movement device 300 is configured to stop, at least in part, relative movement between the elongated needle assembly 202 and the elongated dilator assembly 102. This is done so that the distal puncture device 204 of the elongated needle assembly 202 is held stationary and cannot be movable relative to the elongated dilator assembly 102 (that is, the elongated needle assembly 202 is prevented from moving along the interior of the elongated dilator assembly 102). The stop-movement device 300 is configured to selectively lock the position of the elongated needle assembly 202 to the elongated dilator assembly 102 so that the distal puncture device 204 may be secured (preferably, without having to use the two-finger technique). The stop-movement device 300 provides improved safety for the surgeon and/or the patient during a procedure, such as a transseptal procedure associated with puncturing the fossa ovalis, etc. The stop-movement device 300 may be utilized for any type of puncture formation, such as forming a puncture across the interventricular septum, between blood vessels, a transcaval procedure, a reverse Potts Shunt procedure or the Glenn Shunt procedure, etc., and any equivalent thereof.

Referring to the embodiment as depicted in FIG. 3, when the stop-movement device 300 is positioned to lock the elongated needle assembly 202 with the elongated dilator assembly 102, the elongated needle assembly 202 is not able to be moved inside and along the elongated dilator assembly 102. When the stop-movement device 300 is removed from the elongated dilator assembly 102 and the elongated needle assembly 202 (the stop-movement device 300 is released), the elongated needle assembly 202 (and the distal puncture device 204) are movable inside and along the elongated dilator assembly 102. The sheath assembly 402 is movable along the elongated dilator assembly 102. The stop-movement device 300 is configured to selectively fit tightly around, at least in part, the elongated dilator assembly 102 and the elongated needle assembly 202 (but may be selectively released therefrom, as desired). This is done (preferably) in such a way that the elongated dilator assembly 102 and the elongated needle assembly 202 are selectively locked relative to each other. The stop-movement device 300 includes (preferably) a single component for the body 301. It will be appreciated that the stop-movement device 300 may include multiple pieces that are fitted together (snap fitted, click connected, etc.), for the formation of the body 301 (if desired).

FIG. 4 to FIG. 10 depict side views (FIG. 4, FIG. 5, FIG. 6, FIG. 8 and FIG. 10) and perspective side views (FIG. 7 and FIG. 9) of embodiments of a method of utilizing the stop-movement device 300 of FIG. 2.

Figure 4:
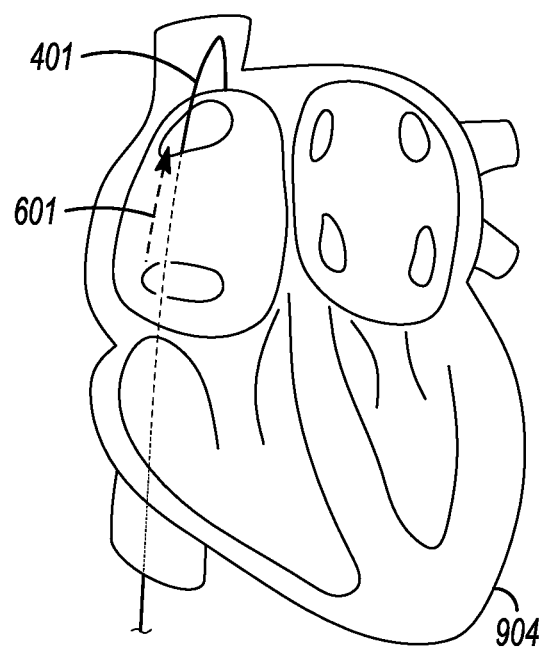
FIG. 4 to FIG. 10 depict side views (FIG. 4, FIG. 5, FIG. 6, FIG. 8 and FIG. 10) and perspective side views (FIG. 7 and FIG. 9) of embodiments of a method of utilizing the stop-movement device of FIG. 2.
Figure 5:
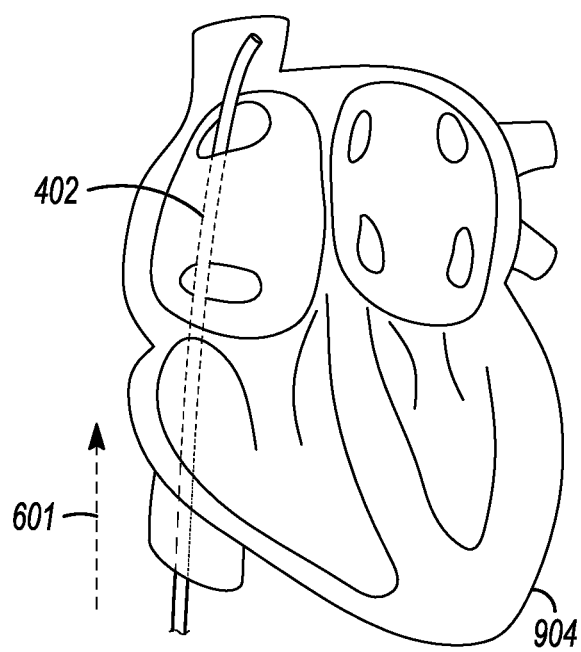
Figure 6:
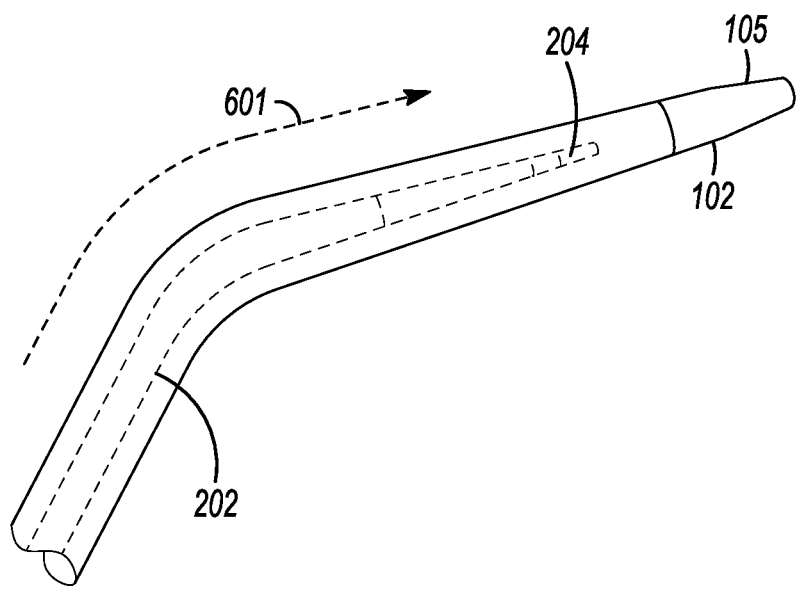
Figure 7:
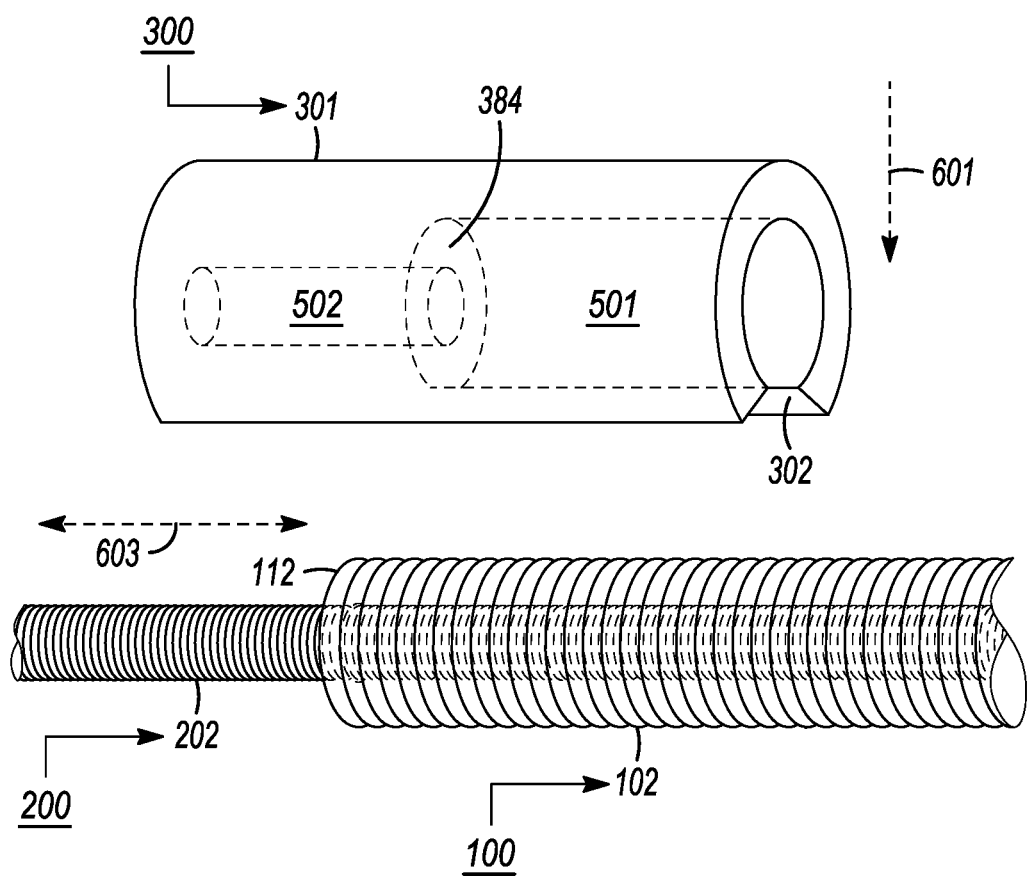
Figure 8:
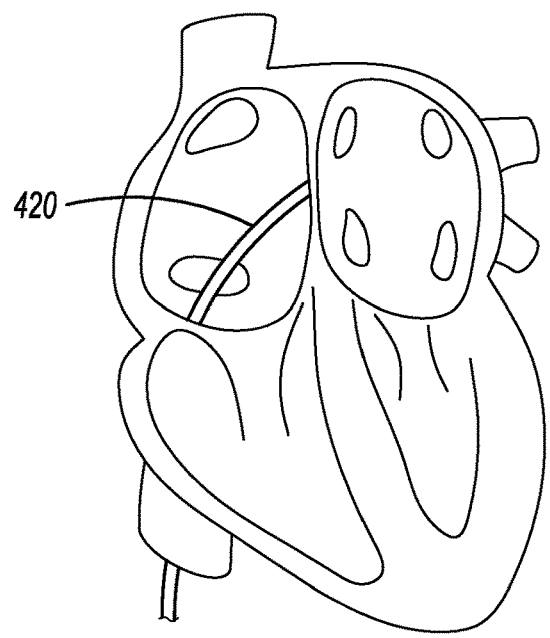

Referring to the embodiments as depicted in FIG. 4 to FIG. 10, there is depicted a method for a procedure. With reference to FIG. 4, the procedure includes advancing the guidewire 401 into a biological feature 904 (such as the superior vena cava of the heart, etc.). With reference to FIG. 5, the procedure includes advancing the elongated dilator assembly 102 and the sheath assembly 402 over the guidewire 401 into the biological feature 904. The procedure also includes removing the guidewire 401 after the elongated dilator assembly 102 and the sheath assembly 402 are positioned as desired. With reference to FIG. 6, the procedure includes advancing the elongated needle assembly 202 having the distal puncture device 204 proximal to the dilator tip 105 of the elongated dilator assembly 102. With reference to FIG. 6, the procedure includes using the stop-movement device 300 to lock the elongated dilator assembly 102 to the elongated needle assembly 202. Locking may be done by pushing the stop-movement device 300 onto the dilator hub portion 104 and a portion of the elongated dilator assembly 102 (as depicted in FIG. 3, if so desired). With reference to FIG. 8, the procedure includes moving (clocking) the elongated needle assembly 202 and the elongated dilator assembly 102 together (in unison) to a desired position (with help from the stop-movement device 300).

Figure 9:
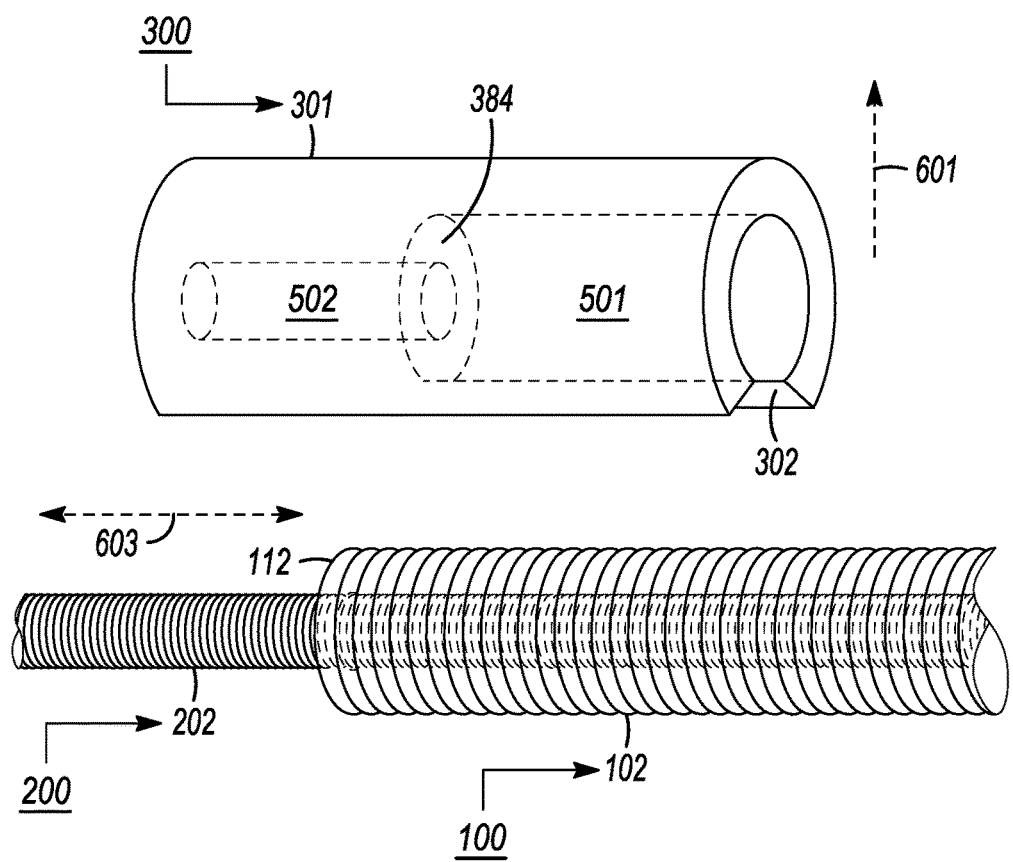

The procedure may include moving the elongated needle assembly 202 and the elongated dilator assembly 102 together to a desired location (such as, the fossa ovalis). The procedure may include tenting the desired biological feature with the distal tip of the elongated needle assembly 202, etc., if so desired. With reference to FIG. 9, the procedure includes removing the stop-movement device 300 (thereby releasing the elongated dilator assembly 102 and the elongated needle assembly 202 from each other); in this manner, once released, the elongated needle assembly 202 may be advanced so that energy may be emitted (applied) to make (form) the puncture 905 (it is understood that the elongated needle assembly 202 forms the puncture, not the elongated dilator assembly 102). Releasing the stop-movement device 300 may be done by pulling the stop-movement device 300 off the dilator hub portion 104 and a portion of the elongated needle assembly 202, etc. The procedure may include continuing with the rest of (the remaining steps of) a procedure (such as, the transseptal puncture procedure, etc.).

Referring to the embodiment as depicted in FIG. 4, a guidewire 401 is advanced (maneuvered) along the first movement direction 601, into a biological feature 904 (such as the superior vena cava of the heart) of a patient. It will be appreciated that for FIG. 0.4, FIG. 5, FIG. 6 and FIG. 10, the first movement direction 601 refers to the motion of advancing the puncture device, whereas for FIG. 7, FIG. 9, and FIG. 13, the first movement direction 601 refers to the motion of moving (pushing down or pulling up) the stop-movement device 300.

Referring to the embodiment as depicted in FIG. 5, the sheath assembly 402 and the dilator assembly 102 are advanced over the guidewire assembly 401 (without the elongated needle assembly 202), then the guidewire assembly 401 is removed, and then the elongated needle assembly 202 is advanced along the sheath assembly 402 and the dilator assembly 102 and into the biological feature (such as a wall or the superior vena cava of the heart, etc.).

Referring to the embodiment as depicted in FIG. 6, the elongated needle assembly 202 with the distal puncture device 204 are advanced, along the first movement direction 601, to a position that is about one (1) centimeter proximal to the dilator tip 105 of the elongated dilator assembly 102.

Referring to the embodiment as depicted in FIG. 7, before installing the stop-movement device 300, the elongated dilator assembly 102 and the elongated needle assembly 202 are movable (freely movable) along an axial movement direction 603. The elongated needle assembly 202 may freely move into the end section 112 of the elongated dilator assembly 102, etc. The stop-movement device 300 defines a first interior zone 501 configured to selectively engage with a portion of the elongated dilator assembly 102. The stop-movement device 300 defines a second interior zone 502 configured to selectively engage with a portion of the elongated needle assembly 202. To install the stop-movement device 300 for locking the elongated dilator assembly 102 and the elongated needle assembly 202 together, the stop-movement device 300 is moved along a first movement direction 601 toward the elongated dilator assembly 102 and the elongated needle assembly 202. This is done so that the receiving portal 302 receives the elongated dilator assembly 102 and the elongated needle assembly 202 (into the first interior zone 501 and the second interior zone 502, respectively). Once the stop-movement device 300 is installed, the elongated dilator assembly 102 and the elongated needle assembly 202 cannot move relative to each other along the axial movement direction 603. The stop-movement device 300 also includes a step 384 positioned between the first interior zone 501 and the second interior zone 502. Once the stop-movement device 300 is installed, the step 384 abuts the end section 112 of the elongated dilator assembly 102.

Referring to the embodiment as depicted in FIG. 8, the sheath assembly 402, the elongated dilator assembly 102 and the elongated needle assembly 202 are moved or rotated (clocked from about the three o'clock position to about the 6 o'clock position, while the stop-movement device 300 remains installed). Then, the sheath assembly 402, the elongated dilator assembly 102 and the elongated needle assembly 202 are moved (pulled) down to a biological wall (such as the fossa ovalis of the heart); this is done in such a way that the top of the sheath assembly 402 (or the elongated dilator assembly 102) tents (elastically deforms) the biological wall (such as, the fossa ovalis, etc.).

Referring to the embodiment as depicted in FIG. 9, after the distal sections of the sheath assembly 402, the elongated dilator assembly 102 and the elongated needle assembly 202 are positioned as desired, the stop-movement device 300 is removed from the elongated dilator assembly 102 and the elongated needle assembly 202. This is done so that the elongated dilator assembly 102 and the elongated needle assembly 202 may become movable (freely movable) along the axial movement direction 603. To remove the stop-movement device 300 for unlocking the elongated dilator assembly 102 and the elongated needle assembly 202 from each other, the stop-movement device 300 is moved along the first movement direction 601 away from the elongated dilator assembly 102 and the elongated needle assembly 202 so that the elongated dilator assembly 102 and the elongated needle assembly 202 become removed from the receiving portal 302 (that is, become removed from the first interior zone 501 and the second interior zone 502, respectively). Once the stop-movement device 300 is removed, the elongated dilator assembly 102 and the elongated needle assembly 202 may move relative to each other along the axial movement direction 603. Once the stop-movement device 300 is removed, the step 384 no longer abuts the end section 112 of the elongated dilator assembly 102.

Figure 10:
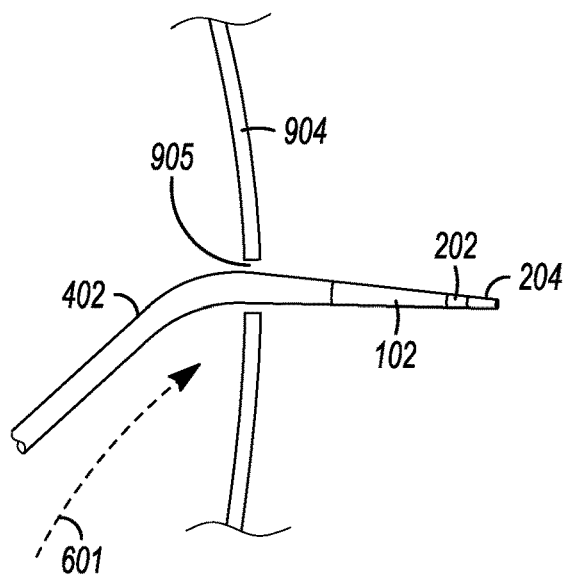

Referring to the embodiment as depicted in FIG. 10, after the stop-movement device 300 is removed from the elongated dilator assembly 102 and the elongated needle assembly 202, the elongated needle assembly 202 may be deployed so that the distal puncture device 204 is utilized for formation of the puncture hole 905. For the case where the distal puncture device 204 includes a mechanical needle, the elongated needle assembly 202 is advanced into the biological feature (such as a biological wall, etc.). For the case where the distal puncture device 204 includes an energy emitting device (such as, a radio frequency emitter, etc., and any equivalent thereof), the energy emitting device is activated to form the puncture hole 905. The remainder of the transseptal puncture procedure may be conducted accordingly.

Referring to the embodiment as depicted in FIG. 3, it will be appreciated that the stop-movement device 300 is configured to accommodate the dimensions of the various types of known puncture devices. The shape of the dilator hub portion 104 may be accommodated.

The stop-movement device 300 may include (preferably) a high-density polyethylene (HDPE). The stop-movement device 300 includes or defines (preferably) the receiving portal 302 (also called a slit) configured to allow the stop-movement device 300 to fit over (at least in part) and locably engage (snap onto) a portion of the elongated dilator assembly 102 and a portion of the elongated needle assembly 202. FIG. 11 to FIG. 14 depict end perspective views (FIG. 11 and FIG. 14), an end view (FIG. 12) and a side perspective view (FIG. 13) of embodiments of the stop-movement device 300 of FIG. 2.

Figure 11:
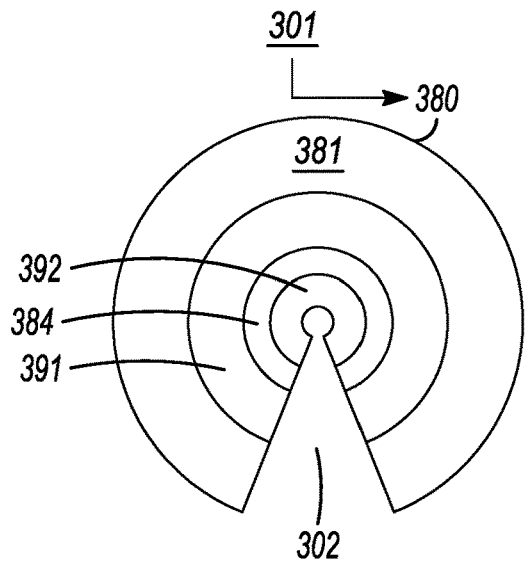
FIG. 11 to FIG. 14 depict end perspective views (FIG. 11 and FIG. 14), an end view (FIG. 12) and a side perspective view (FIG. 13) of embodiments of the stop-movement device of FIG. 2.
Figure 12:
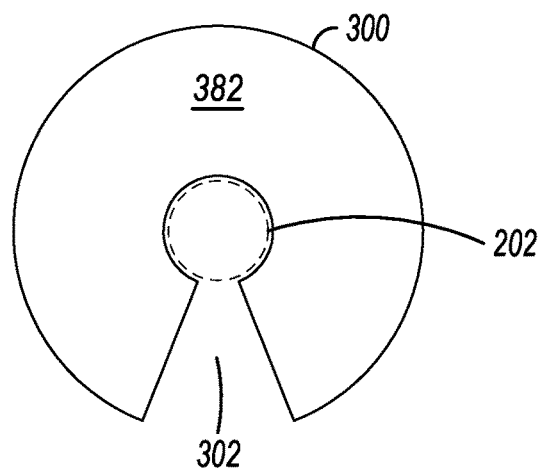

Referring to the embodiments as depicted in FIG. 11 and FIG. 12, the body 301 (of the stop-movement device 300) includes (preferably) a single body member 380. The single body member 380 includes a first end face 381 and a second end face 382. The first end face 381 is configured to be positioned over (at least in part) the elongated dilator assembly 102 (as depicted in FIG. 3). The second end face 382 is configured to be positioned over (at least in part) the elongated needle assembly 202 (as depicted in FIG. 3). The single body member 380 also includes a step 384 positioned between the first end face 381 and the second end face 382. The single body member 380 also includes a first inner wall surface 391 configured to (frictionally engage) contact the outer surface of the elongated dilator assembly 102 (as depicted in FIG. 3). The single body member 380 also includes a second inner wall surface 392 configured to (frictionally engage) contact the outer surface of the elongated needle assembly 202 (as depicted in FIG. 3). The receiving portal 302 (also called an axial groove) is aligned coaxially with a longitudinal axis. The receiving portal 302 extends between opposite end sections of the single body member 380 (or the body 301) or the opposite end faces of the single body member 380 (or the body 301), etc.

Figure 13:
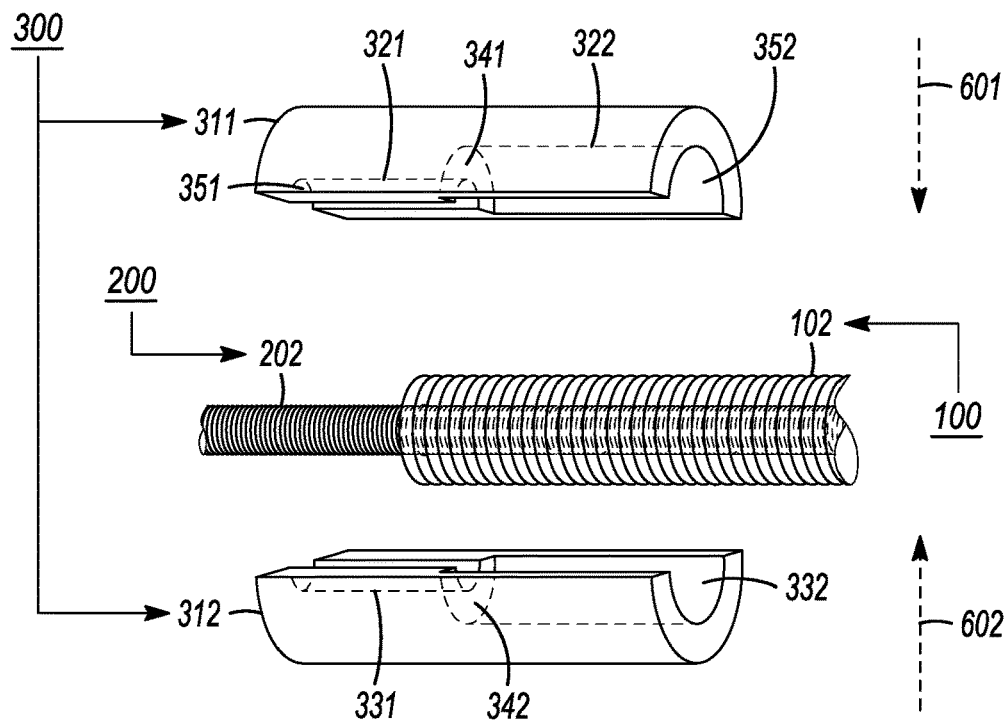
Figure 14:
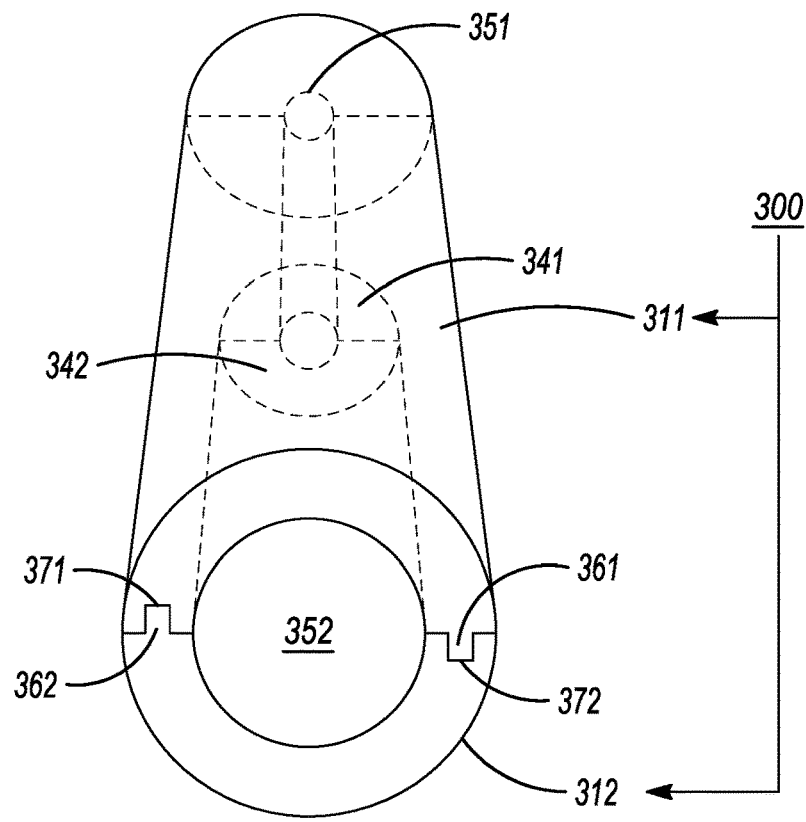

Referring to the embodiments as depicted in FIG. 13 and FIG. 14, the stop-movement device 300 includes a first body 311 and a second body 312. The second body 312 is configured to be selectively mated and connected (snap fitted together) to the first body 311. The first body 311 and the second body 312 may be separately friction fitted (engaged) to portions of the elongated dilator assembly 102 and the elongated needle assembly 202. The first body 311 is movable along a first movement direction 601 to meet up, and selectively mate (interface) with, the second body 312. Alternatively, the second body 312 is movable along a second movement direction 602 to meet up, and selectively mate (interface) with, the first body 311. The first body 311 defines a first body cavity 321 configured to contact a portion of the elongated needle assembly 202.

The first body 311 defines a first body groove 322 configured to contact a portion of the elongated dilator assembly 102. The first body cavity 321 and the first body groove 322 are in fluid communication with each other. A first step 341 is located between the first body cavity 321 and the first body groove 322. The second body 312 defines a second body cavity 331 configured to contact a portion of the elongated needle assembly 202. The second body 312 defines a second body groove 332 configured to contact a portion of the elongated dilator assembly 102. The second body cavity 331 and the second body groove 332 are in fluid communication with each other. A second step 342 is located between the first body cavity 321 and the first body groove 322. The first body cavity 321 and the second body cavity 331 are configured to face each other after the second body 312 is selectively mated and connected to the first body 311. The first body groove 322 and the second body groove 332 are configured to face each other after the second body 312 is selectively mated and connected to the first body 311. The first step 341 and the second step 342 are coplanar after the second body 312 is selectively mated and connected to the first body 311. The first body 311 and the second body 312 cooperate to define a first entrance 351 leading into the first body cavity 321 and the second body cavity 331 (after the second body 312 is selectively mated and connected to the first body 311). The first body 311 and the second body 312 cooperate (once mated together) to define a second entrance 352 leading into the second body groove 332 and the first body groove 322 (after the second body 312 is selectively mated and connected to the first body 311). The first body 311 provides a first connection protrusion 361. The second body 312 provides a second connection protrusion 362. The first body 311 provides a first connection groove 371. The second body 312 provides a second connection groove 372. The first connection protrusion 361 is configured to be securely received into the second connection groove 372. The second connection protrusion 362 is configured to be securely received into the first connection groove 371.

The following is offered as further description of the embodiments, in which any one or more of any technical feature (described in the detailed description, the summary and the claims) may be combinable with any other one or more of any technical feature (described in the detailed description, the summary and the claims). It is understood that each claim in the claims section is an open ended claim unless stated otherwise. Unless otherwise specified, relational terms used in these specifications should be construed to include certain tolerances that the person skilled in the art would recognize as providing equivalent functionality. By way of example, the term perpendicular is not necessarily limited to 90.0 degrees, and may include a variation thereof that the person skilled in the art would recognize as providing equivalent functionality for the purposes described for the relevant member or element. Terms such as "about" and "substantially", in the context of configuration, relate generally to disposition, location, or configuration that are either exact or sufficiently close to the location, disposition, or configuration of the relevant element to preserve operability of the element within the disclosure which does not materially modify the disclosure. Similarly, unless specifically made clear from its context, numerical values should be construed to include certain tolerances that the person skilled in the art would recognize as having negligible importance as they do not materially change the operability of the disclosure. It will be appreciated that the description and/or drawings identify and describe embodiments of the apparatus (either explicitly or inherently). The apparatus may include any suitable combination and/or permutation of the technical features as identified in the detailed description, as may be required and/or desired to suit a particular technical purpose and/or technical function. It will be appreciated that, where possible and suitable, any one or more of the technical features of the apparatus may be combined with any other one or more of the technical features of the apparatus (in any combination and/or permutation). It will be appreciated that persons skilled in the art would know that the technical features of each embodiment may be deployed (where possible) in other embodiments even if not expressly stated as such above. It will be appreciated that persons skilled in the art would know that other options may be possible for the configuration of the components of the apparatus to adjust to manufacturing requirements and still remain within the scope as described in at least one or more of the claims. This written description provides embodiments, including the best mode, and also enables the person skilled in the art to make and use the embodiments. The patentable scope may be defined by the claims. The written description and/or drawings may help to understand the scope of the claims. It is believed that all the crucial aspects of the disclosed subject matter have been provided in this document. It is understood, for this document, that the word "includes" is equivalent to the word "comprising" in that both words are used to signify an open-ended listing of assemblies, components, parts, etc. The term "comprising", which is synonymous with the terms "including," "containing," or "characterized by," is inclusive or open-ended and does not exclude additional, unrecited elements or method steps. Comprising (comprised of) is an "open" phrase and allows coverage of technologies that employ additional, unrecited elements. When used in a claim, the word "comprising" is the transitory verb (transitional term) that separates the preamble of the claim from the technical features of the disclosure. The foregoing has outlined the non-limiting embodiments (examples). The description is made for particular non-limiting embodiments (examples). It is understood that the non-limiting embodiments are merely illustrative as examples.

What is claimed is:

1. An apparatus, comprising:
   an elongated dilator assembly defining a lumen; and
   an elongated needle assembly configured to be receivable and movable within the lumen; and
   a stop-movement device having a generally cylindrical body defining a longitudinal interior passage including,
      a first inner wall surface having a first interior dimension and configured to engage a portion of the elongated dilator assembly,
      a second inner wall surface adjacent the first inner wall surface, the second inner wall surface having a second interior dimension and configured to engage a portion of the elongated needle assembly, the first interior dimension being greater than the second interior dimension, and
      a step disposed in the interior passage at an intersection of the first and second inner wall surfaces and configured to be mounted to the elongated needle assembly and the elongated dilator assembly after the elongated needle assembly, in use, is received, at least in part, inside the lumen of the elongated dilator assembly; and
   wherein the step of the stop-movement device is configured to contact a proximal end of the elongated dilator assembly so as to inhibit relative movement between the elongated needle assembly and the elongated dilator assembly in a distal direction.

2. The apparatus of claim 1, wherein: the elongated dilator assembly is configured to be received in a sheath assembly.

3. The apparatus of claim 1, wherein: the stop-movement device includes an elastically deformable material.

4. The apparatus of claim 1, wherein:
   the stop-movement device is configured to selectively receive, at least in part, and hold onto the elongated dilator assembly and the elongated needle assembly; and
   the stop-movement device is configured to selectively release from the elongated dilator assembly and the elongated needle assembly.

5. The apparatus of claim 1, wherein: the stop-movement device is configured to be friction fitted, at least in part, to a portion of an outer surface of the elongated needle assembly.

6. The apparatus of claim 1, wherein: the stop-movement device is configured to be friction fitted, at least in part, to a portion of an outer surface of the elongated dilator assembly.

7. The apparatus of claim 1, wherein:
   the second inner wall surface is shaped to fit around, at least in part, a portion of an outer diameter of the elongated needle assembly; and
   the first inner wall surface is shaped to fit around, at least in part, a portion of an outer diameter of the elongated dilator assembly.

8. The apparatus of claim 1, wherein:
   the elongated needle assembly is not able to be moved inside and along the elongated dilator assembly after the stop-movement device is positioned to lock the elongated needle assembly with the elongated dilator assembly; and
   the elongated needle assembly is movable inside, and along, the elongated dilator assembly after the stop-movement device is removed from the elongated dilator assembly and the elongated needle assembly.

9. The apparatus of claim 1, wherein: the stop-movement device is configured to selectively fit tightly around, at least in part, the elongated dilator assembly and the elongated needle assembly in such a way that the stop-movement device, in use, selectively locks the elongated dilator assembly and the elongated needle assembly to each other.

10. The apparatus of claim 1, wherein: the stop-movement device is configured to fit over, at least in part, and lockably engage, at least in part, the elongated dilator assembly and the elongated needle assembly.

11. The apparatus of claim 1, wherein: the body of the stop-movement device includes a single body member including the first inner wall surface and is configured to frictionally engage a portion of the elongated dilator assembly; and the single body member also includes the second inner wall surface and is configured to frictionally engage a portion of the elongated needle assembly.

12. The apparatus of claim 1, wherein: the body of the stop-movement device includes: a first body portion defining a first body cavity configured to contact a portion of the elongated needle assembly, a first body groove configured to contact a portion of the elongated dilator assembly and a first step located between the first body cavity and the first body groove; and a second body portion configured to be selectively coupled to the first body portion;
   wherein the first body cavity and the first body groove are in fluid communication with each other.

13. The apparatus of claim 12, wherein:
   the second body portion defines a second body cavity configured to contact a portion of the elongated needle assembly;
   the second body portion defines a second body groove configured to contact a portion of the elongated dilator assembly;
   the second body cavity and the second body groove are in fluid communication with each other; and
   the second body portion includes a second step located between the second body cavity and the first body groove.

14. The apparatus of claim 13, wherein:
   the first body cavity and the second body cavity are configured to face each other after the second body portion is selectively mated and connected to the first body portion; and
   the first body groove and the second body groove are configured to face each other after the second body portion is selectively mated and connected to the first body portion; and
   the first step and the second step are coplanar after the second body portion is selectively mated and connected to the first body portion.

15. The apparatus of claim 14, wherein:
   the first body portion and the second body portion cooperate to define:

a first entrance leading into the first body cavity and the second body cavity after the second body portion is selectively mated and connected to the first body portion; and a second entrance leading into the second body groove and the first body groove after the second body portion is selectively mated and connected to the first body portion.

16. The apparatus of claim 15, wherein:

the first body portion provides a first connection protrusion;

the second body portion provides a second connection protrusion;

the first body portion provides a first connection groove;

the second body portion provides a second connection groove, the first connection protrusion is configured to be securely received into the second connection groove; and the second connection protrusion is configured to be securely received into the first connection groove.

* * * * *